United States Patent [19]

Kappel et al.

[11] Patent Number: 5,716,387
[45] Date of Patent: Feb. 10, 1998

[54] WARMING BLANKET FOR PEDIATRIC USE

[75] Inventors: Thomas F. Kappel, St. Louis; Dennis S. Chivetta; Scott D. Dickerhoff, both of Ballwin; Philip M. Metzler, St. Charles, all of Mo.

[73] Assignee: Mallinckrodt Medical, Inc., St. Louis, Mo.

[21] Appl. No.: 680,114

[22] Filed: Jul. 15, 1996

Related U.S. Application Data

[60] Continuation of Ser. No. 463,652, Jun. 5, 1995, abandoned, which is a division of Ser. No. 187,561, Jan. 26, 1994, abandoned.

[51] Int. Cl.⁶ ........................................ A61F 7/00
[52] U.S. Cl. .................. 607/107; 607/114; 126/204; 62/259.003; 5/423
[58] Field of Search .................. 5/421-3, 482, 5/485; 607/104, 107; 165/46; 126/204; 62/259.003

[56] References Cited

U.S. PATENT DOCUMENTS

| | | |
|---|---|---|
| 630,565 | 8/1899 | Safran . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber . |
| 2,791,168 | 5/1957 | Mauch . |
| 2,834,033 | 5/1958 | O'Brien . |
| 2,998,817 | 9/1961 | Armstrong . |
| 3,034,132 | 5/1962 | Landsberger et al. . |
| 3,307,554 | 3/1967 | Thornton et al. . |
| 3,308,850 | 3/1967 | Gill . |
| 3,610,251 | 10/1971 | Sanderson . |
| 3,674,034 | 7/1972 | Hardy . |
| 3,740,777 | 6/1973 | Dee . |
| 3,757,366 | 9/1973 | Sacher . |
| 3,844,339 | 10/1974 | Kranz . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,653,131 | 3/1987 | Diehl . |
| 4,660,388 | 4/1987 | Greene, Jr. . |
| 4,777,802 | 10/1988 | Feher . |
| 4,807,644 | 2/1989 | Sandhaus . |
| 4,867,230 | 9/1989 | Voss .................... 5/423 |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 11/1931 | Switzerland . |
| 85 03216 | 8/1985 | WIPO . |
| 94 03131 | 2/1994 | WIPO . |
| 95 20371 | 8/1995 | WIPO . |
| 95 35077 | 12/1995 | WIPO . |
| 96 03098 | 2/1996 | WIPO . |

*Primary Examiner*—Robert L. Nasser
*Attorney, Agent, or Firm*—Rothwell, Figg, Ernst & Kurz P.C.

[57] ABSTRACT

The present invention relates to a blanket for use with forced air convection systems, wherein the blanket is sized to accommodate pediatric patients. The blankets according to the present invention may be used both over or under the patient, thereby facilitating use in the operating room or outside the operating room. The present invention also relates to a blanket for use with forced air convection systems which is nonflammable and laser resistant. In addition, the present invention relates to methods of prevention hypothermia and hyperthermia and to a method of making a blanket for use with forced air convection systems.

14 Claims, 5 Drawing Sheets

U.S. PATENT DOCUMENTS

| | | |
|---|---|---|
| 4,959,877 | 10/1990 | Covil . |
| 4,997,230 | 3/1991 | Spitalnick . |
| 5,022,110 | 6/1991 | Stroh . |
| 5,044,364 | 9/1991 | Crowther . |
| 5,097,548 | 3/1992 | Heck et al. . |
| 5,106,373 | 4/1992 | Augustine et al. . |
| 5,125,238 | 6/1992 | Ragan et al. ................................. 5/423 |
| 5,165,400 | 11/1992 | Berke . |
| 5,184,612 | 2/1993 | Augustine . |
| 5,265,599 | 11/1993 | Stephenson et al. ........................ 5/423 |
| 5,300,098 | 4/1994 | Philipot . |
| 5,300,100 | 4/1994 | Hickle et al. . |
| 5,300,101 | 4/1994 | Augustine et al. ..................... 607/107 |
| 5,300,102 | 4/1994 | Augustine et al. . |
| 5,304,213 | 4/1994 | Berke et al. . |
| 5,304,217 | 4/1994 | Stephenson et al. . |
| 5,318,568 | 6/1994 | Kaufmann et al. . |
| 5,324,320 | 6/1994 | Augustine et al. . |
| 5,336,250 | 8/1994 | Augustine . |
| 5,343,579 | 9/1994 | Dickerhoff et al. ........................ 5/423 |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani . |
| 5,405,371 | 4/1995 | Augustine et al. . |
| 5,408,712 | 4/1995 | Brun . |
| 5,443,488 | 8/1995 | Namenye et al. . |

5,716,387

WARMING BLANKET FOR PEDIATRIC USE

This is a continuation of application Ser. No. 08/463,652 filed Jun. 5, 1995, now abandoned which was a division of application Ser. No. 08/187,561 filed Jan. 26, 1994 now abandoned.

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. In the operating room, the hypothermic condition may be brought on by many factors including anesthesia, the air conditioning of the operating room, and the infusion of cold blood, I-V solutions, or irrigating fluids. Hypothermia is also a problem in the recovery room or PACU, as well as other areas in a hospital where room temperatures are kept cool and infusions of blood or other fluids may continue.

The prevention of hypothermia is especially important for pediatric care, because pediatric patients may be adversely effected by small changes in temperature. In particular, pediatric patients lose heat faster than adult patients because of their relatively low skin surface area to body mass ratio. Conversely, pediatric patients can also gain heat faster than adult patients. Therefore, pediatric patients are more susceptible to surgical complications, such as catching colds, from slight changes in temperature.

Several methods and products have been developed to help prevent hypothermia from occurring; such as the use of infrared lamps, cotton blankets, and warmwater mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling air flow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine et al, a forced air convection systemm which can supply either cool or warm air to a blanket is described. The blanket in Augustine et al comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss. Each of these patents describe blankets having various attributes and configurations to supply cool or warm air to the person.

While some of the above systems suggest use in the operating room, they all possess similar disadvantages for such use. In particular, for the system to work in the operating room, the blanket must be attached to an air supply or blower unit through a hose. The placement of the hose during surgery can be crucial, as full access to the patient can be compromised if the hose must be located in a position which the surgeon, anesthesiologist or other surgical team member wants to occupy. In addition, the placement of the hose can create difficulties in locating other equipment such as I-V stands, monitors, etc. necessary for the surgical procedure. Moreover, it is important that the hose be as short as possible, because longer hoses lose more heat before delivery to the blanket, and thus overall effectiveness of the blanket is reduced.

Hose placement is not as critical in a non-operating room setting such as the PACU, ICU, or standard hospital room, but it is still desirable to have options for hose placement. This is especially true regarding the interspacial relationships between the blower unit and other equipment such as I-V stands, etc.

The prevention of hypothermia in pediatric patients requires special features and specifications. For purposes of this application, the term "pediatric" will be used to describe a number of patients, including neonates, infants, and children. In particular, the size of pediatric patients require that a relatively small blanket be provided which will still provide all of the warming advantages of a larger adult-sized blanket. Further, in certain surgical procedures, it is desirable to have the pediatric patient lie on top of the blanket because then the blanket is not in the way of the surgeon or other surgical team member. This requires the blanket to have sufficient air flow through the blanket to provide the warming therapy needed to prevent hypothermia.

None of the prior art noted above mentions use of blankets for pediatric patient care. Therefore, there remains a need in the art for improvements to forced warm air convection systems, especially for blankets which can be used in the treatment of pediatric patients.

OBJECTS OF THE INVENTION

It is one object of the present invention to provide a blanket for a forced warm air convection system that may be used specifically for pediatric patients.

It is another object of the present invention to provide a blanket for a forced warm air convection system that may be used over or under a pediatric patient.

It is a further object of the present invention to provide a blanket for a forced warm air convection system that allows placement of a blower and an air supply hose to be selectively chosen depending on the needs of the surgical procedure to be performed.

It is also an object of the present invention to provide a blanket for a forced warm air convection system that is nonflammable and laser resistant.

SUMMARY OF THE INVENTION

The above objects and others are accomplished according to the present invention by providing a blanket for a warmair convection system having a size suitable for a pediatric patient and which includes means to provide enough air flow to accomplish the desired warming therapy.

DETAILED DESCRIPTION OF THE INVENTION

The present invention relates primarily to the prevention of hypothermia in pediatric patients. In particular, the present invention relates to warm air convection blankets for providing warm air to pediatric patients undergoing surgical or other medical procedures. The blankets according to the present invention are designed to by used primarily for pediatric patients from newborn to about five years of age and weights from about five to about fifty pounds.

In addition, the blankets according to the present invention are designed in such a manner that a particular blanket could be used to warm either the upper body, including the head, of a patient, the lower body of the patient, or the entire body of the patient. It is desirable that temperature distribution across the blanket not vary by more than about 5° C. This is accomplished in the blankets according to the present invention, because the blankets can be used for relatively high air temperature distribution at relatively high airflow.

Figure 1:
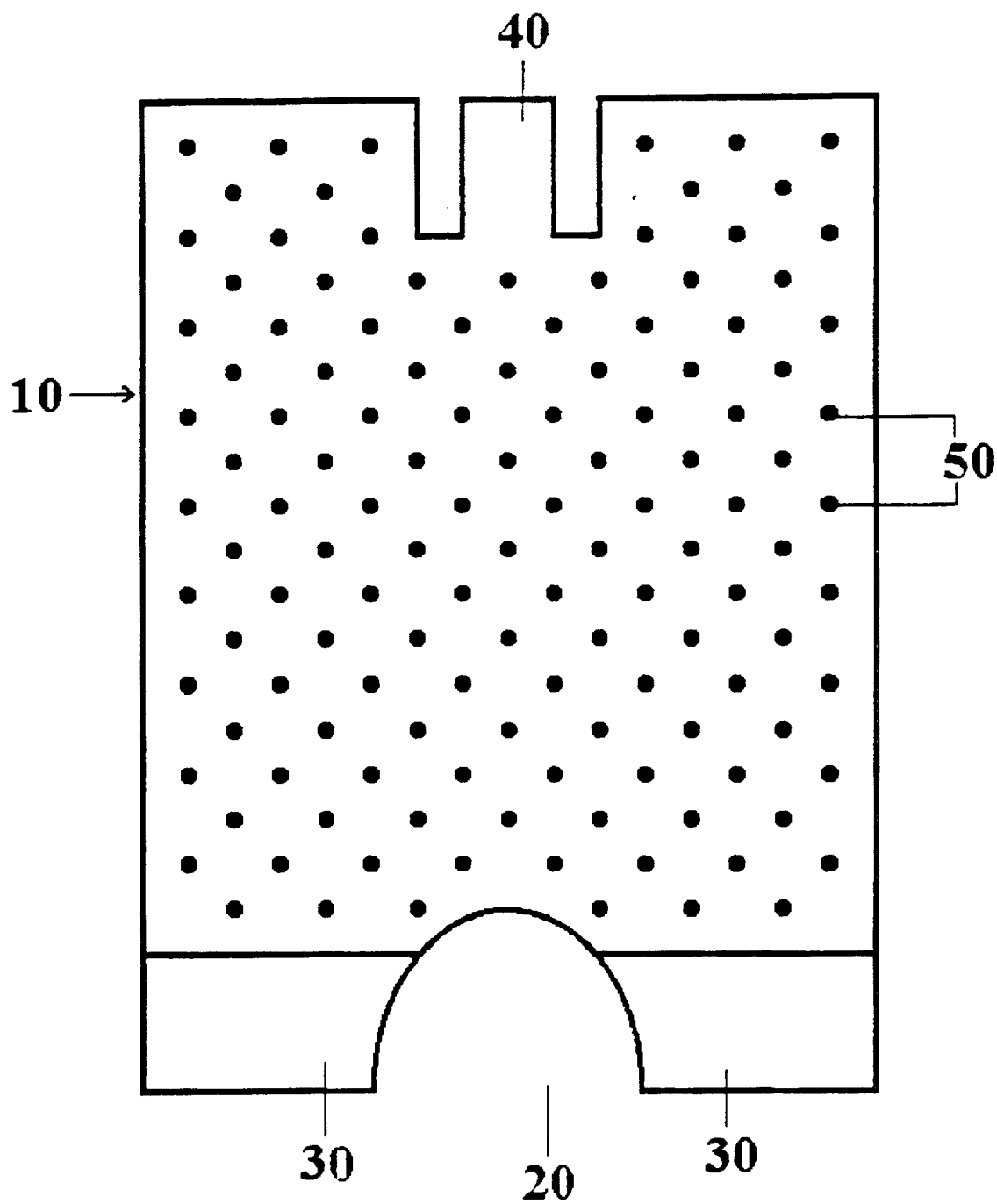
FIG. 1 is a plan view of a blanket for a forced warm air convection system for use primarily in non-operating room settings according to one embodiment of the present invention.

FIG. 1 is a plan view of a blanket, generally designated by reference numeral 10, for a forced warm air convection system, wherein the blanket 10, is appropriate for use primarily outside the operating room. The blanket 10, has a generally rectangular shape and include a head recess portion 20, and shoulder extensions 30. The blanket 10, comprises two sheets of material which are sealed together along their peripheral edges and are connected together at connection spot welds 50, discretely located on the interior surface portions of the sheets. By connecting the sheets of the blanket 10, in this manner, the blanket 10, may be inflated by supplying air to an air chamber formed between the sheets of material.

The blanket 10, further includes an inlet port 40, which communicates with the air chamber of the blanket 10, and may be used to supply air to the air chamber of the blanket 10, so as to inflate blanket 10. One sheet of the blanket 10, is provided with a plurality of small exit perforations 70, (FIG. 4) to allow warm air to escape from the blanket 10, toward a patient.

In use, the blanket 10, is placed over the body of a patient so that the patient's head remains exposed within the head recess portion 20, and the inlet port 40, is located at the feet of the patient. The blanket 10, should be placed such that the sheet having perforations 70, faces the patient. The shoulder extensions 30, are draped over the shoulders of the patient and then tucked under the patients' shoulders to secure the blanket 10, in place. Once the blanket 10, is in place, the blanket 10, may be inflated with warm air through inlet port 40. The warm air is constantly supplied to the air chamber of blanket 10, through inlet port 40, and exits the blanket 10, through the perforations 70, to provide warming therapy to the patient.

The inlet port 40, may initially be closed by any suitable means such as sealing, folding, taping, snapping, etc. In the case where the inlet has been permanently sealed, means such as a perforated tear strip or punch out panel may be provided to enable easy opening of the inlet port selected for use. As an alternative, the inlet may simply be cut open with scissors or a knife.

Alternatively, the inlet port 40, may be initially closed by means that allow for reversibly opening and reclosing. In particular, means such as an adhesive strip or label, double-sided tape, snaps, zippers, folding flaps, folding wire or plastic bars, a ziplock type seal, or hook and loop type fastener, etc. may be utilized. In the alternative, a rubber, elastic, or plastic band could be used to tighten the material of the inlet port 40, around a nozzle inserted therein for supplying air to the interior of the blanket 10.

The perforations 70, formed through one sheet of the blanket 10, are formed by a punching procedure which forms clean, even holes. This method provides a blanket having consistent air flow characteristics. In contrast, perforations of prior art blankets are normally ripped or cut through the lower surface of the blanket which leaves ragged, uneven holes and contributes to widely varying air flow patterns.

Figure 4:
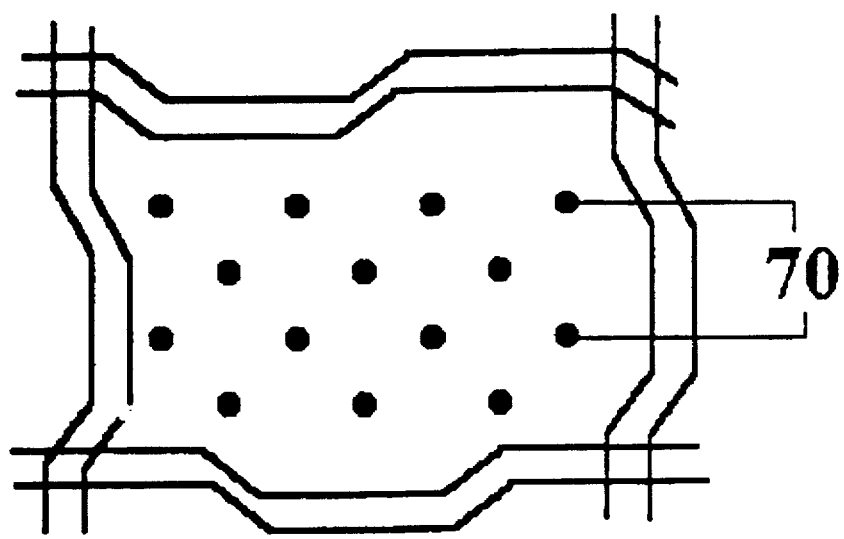
FIG. 4 is a plan view of a portion of a blanket for a forced warm air convection system showing the perforation pattern according to an embodiment of the present invention.

As shown in FIG. 4, perforations 70, are formed in off-set rows. The perforations 70, in a given row extend across the entire width of the blanket, and multiple rows of perforations 70, extend across the entire length of the blanket. Adjacent rows of perforations are offset in such a manner that a perforation in any given row occurs midway between adjacent perforations in an adjacent row of perforations. Preferably, the distance between adjacent rows of perforations 70, is about 1 and ⅛ inches and the distance between adjacent perforations 70, in the same row is about 1 and ¼ inches.

While the blanket 10, has been described as being for use primarily outside the operating room, it should be noted that the blanket 10, may also be appropriate for use in the operating room.

Figure 2:
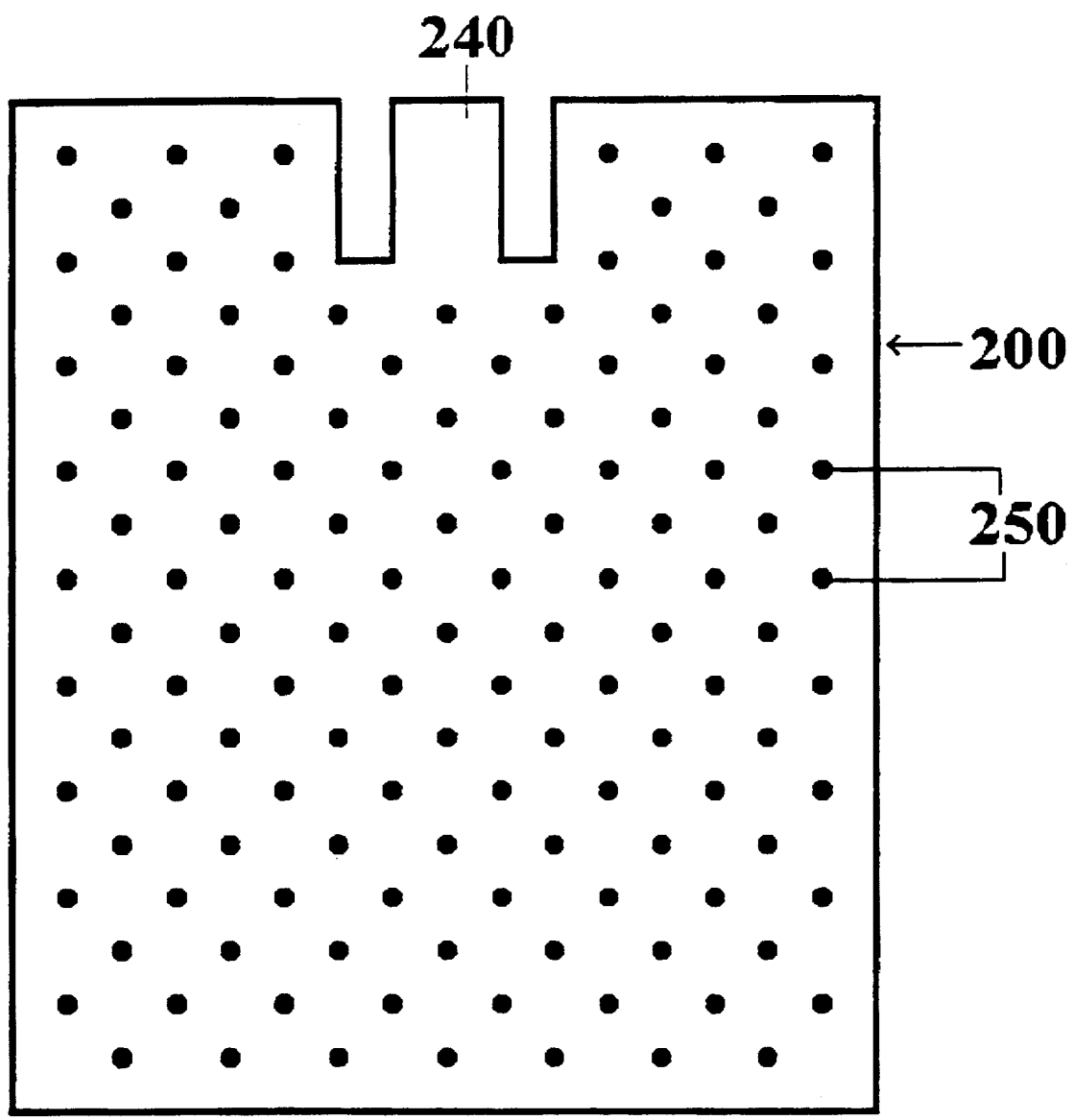
FIG. 2 is a plan view of a blanket for a forced warm air convection system for use primarily in the operating room according to another embodiment of the present invention.

FIG. 2 is a plan view of a blanket, generally designated by reference numeral 200, for a forced warm air convection system, wherein the blanket 200, is appropriate for use primarily in the operating room. The blanket 200, is very similar to the blanket 10, described above, having a generally rectangular shape but does not include a head recess portion or shoulder extensions. The blanket 200, comprises two sheets of material which are sealed together along their peripheral edges and are connected together at connection spot welds 250, discretely located on the interior surface portions of the sheets. By connecting the sheets of the blanket 200, in this manner, the blanket 200, may be inflated by supplying air to an air chamber formed between the sheets of material.

The blanket 200, further includes an inlet port 240, which communicates with the air chamber of the blanket 200, and may be used to supply air to the air chamber of the blanket 200, so as to inflate blanket 200. One sheet of the blanket 200, is provided with a plurality of small exit perforations 70, (FIG. 4) to allow warm air to escape from the blanket 200, toward a patient.

In use, the blanket 200, is placed over or under the body of a patient. When placed over the patient, the blanket 200, is placed so that the sheet having perforations 70, faces the patient and so that the area of the patient upon which surgery or other procedures will be performed remains exposed. The blanket 200, may be situated such that inlet port 240, is located at the feet or at the head of the patient. Once the blanket 200, is in place, the blanket 200, may be inflated with warm air through inlet port 240. The warm air is constantly supplied to the air chamber of blanket 200, through inlet port 240, and exits the blanket 200, through the perforations 70, to provide warming therapy to the patient.

The inlet port 240, may initially be closed using any of the means noted above with respect to inlet port 40, of blanket 10. The perforations 70, formed through one sheet of the blanket 200, are formed by the same punching procedure described above with respect to blanket 10.

While the blanket 200, has been described as being for use primarily in the operating room, it should be noted that the blanket 200, may also be appropriate for use outside the operating room.

When placing blankets under patients, it is often the case that the weight of the patient will cause air flow to be partially or completely restricted through certain portions of the blanket. Therefore, it is desirable to include means of providing for greater and more consistent air flow through the blanket in order to supply the same amount of warming therapy to the patient.

Figure 3:
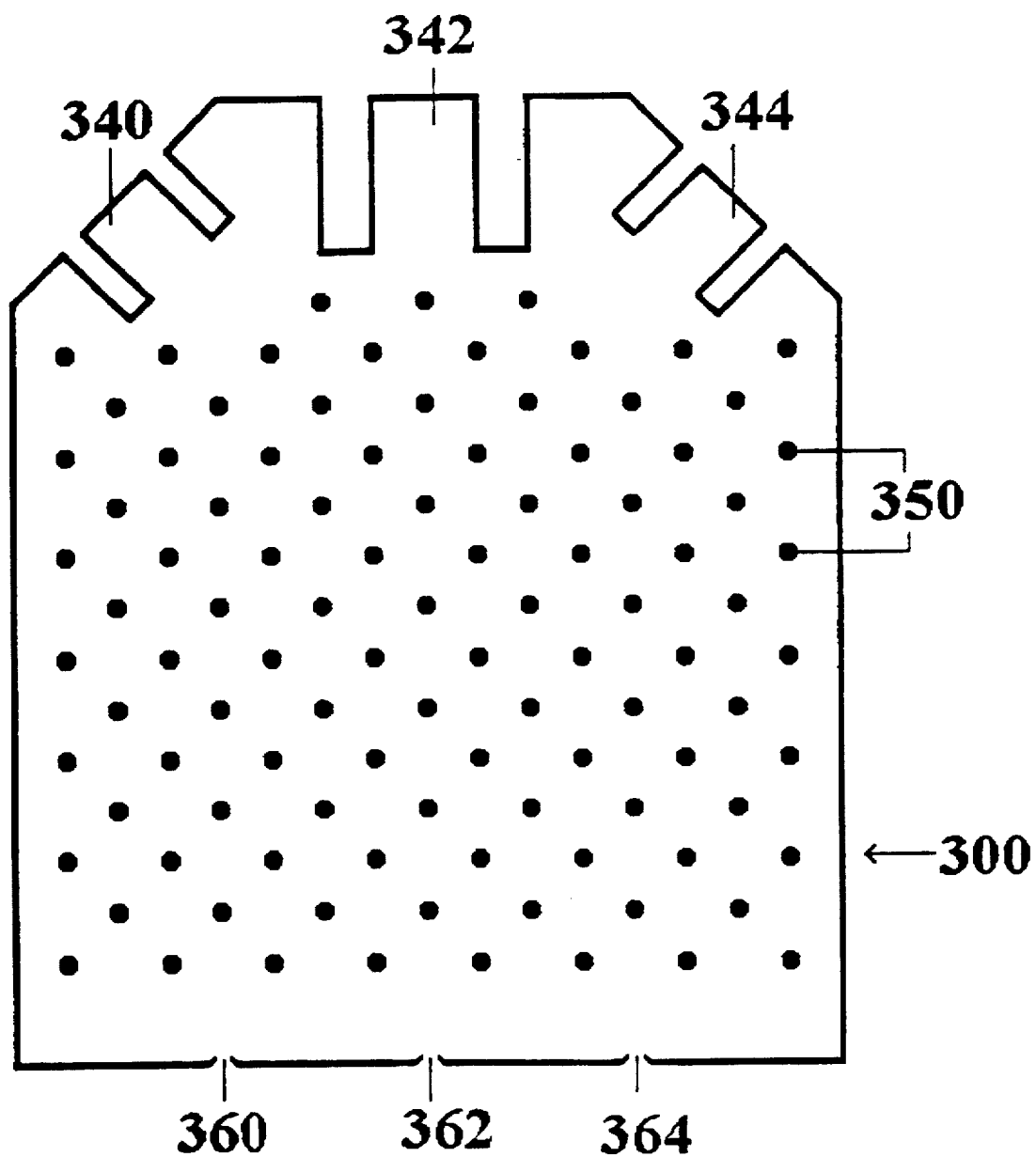
FIG. 3 is a view of a blanket for a forced warm air convection system for use primarily in the operating room according to a further embodiment of the present invention.

FIG. 3 is a plan view of a blanket, generally designated by reference numeral 300, for a forced warm air convection system, wherein the blanket 300, is appropriate for use primarily in the operating room. The blanket 300, is very similar to the blanket 10, described above, having a generally rectangular shape and comprising two sheets of material which are sealed together along their peripheral edges and are connected together at connection spot welds 350, discretely located on the interior surface portions of the sheets. By connecting the sheets of the blanket 300, in this manner, the blanket 300, may be inflated by supplying air to an air chamber formed between the sheets of material.

The blanket 300, further includes three separate inlet ports 340, 342, and 344, which communicate with the air chamber of the blanket 300, and may be used to supply air to the air chamber of the blanket 300, so as to inflate blanket 300. One sheet of the blanket 300, is provided with a plurality of small exit perforations 70, (FIG. 4), to allow warm air to escape from the blanket 300, toward a patient. In addition, blanket 300, includes three exit vents 360, 362, and 364, which communicate with the air chamber of the blanket 300, and which allow warm air to escape from the blanket 300.

In use, the blanket 300, may be placed over or under the body of a patient, but is preferably placed under the patient. When placed under the patient, the blanket 300, is placed so that the sheet having perforation 70, is facing the patient. The blanket 300, may be situated such that inlet ports 340, 342, and 344 are located at the feet or at the head of the patient. Once the blanket 300, is in place, the blanket 300, may be inflated with warm air through any one of inlet ports 340, 342, or 344, or may be inflated through more than one inlet port if so desired. The warm air is constantly supplied to the air chamber of blanket 300, through the selected inlet port and exits the blanket 300, through the perforations 70, to provide warming therapy to the patient and also through the vents 360, 362, and 364, to increase air flow through the blanket 300. By providing multiple inlet ports and exit vents, the circulating warm air has more pathways to move through the blanket and thus provide a greater and more consistent airflow through the blanket. Therefore, more consistent warming therapy can be provided to the patient, even in the event that air flow is partially or completely restricted through certain portions of the blanket 300.

The inlet ports 340, 342, and 344, may initially be closed using any of the means noted above with respect to inlet port 40, of blanket 10. The perforations formed through the one sheet of the blanket 300, are formed by the same punching procedure described above with respect to blanket 10.

While the blanket 300, has been described as being for use primarily in the operating room, it should be noted that the blanket 300, may also be appropriate for use outside the operating room.

Figure 5:
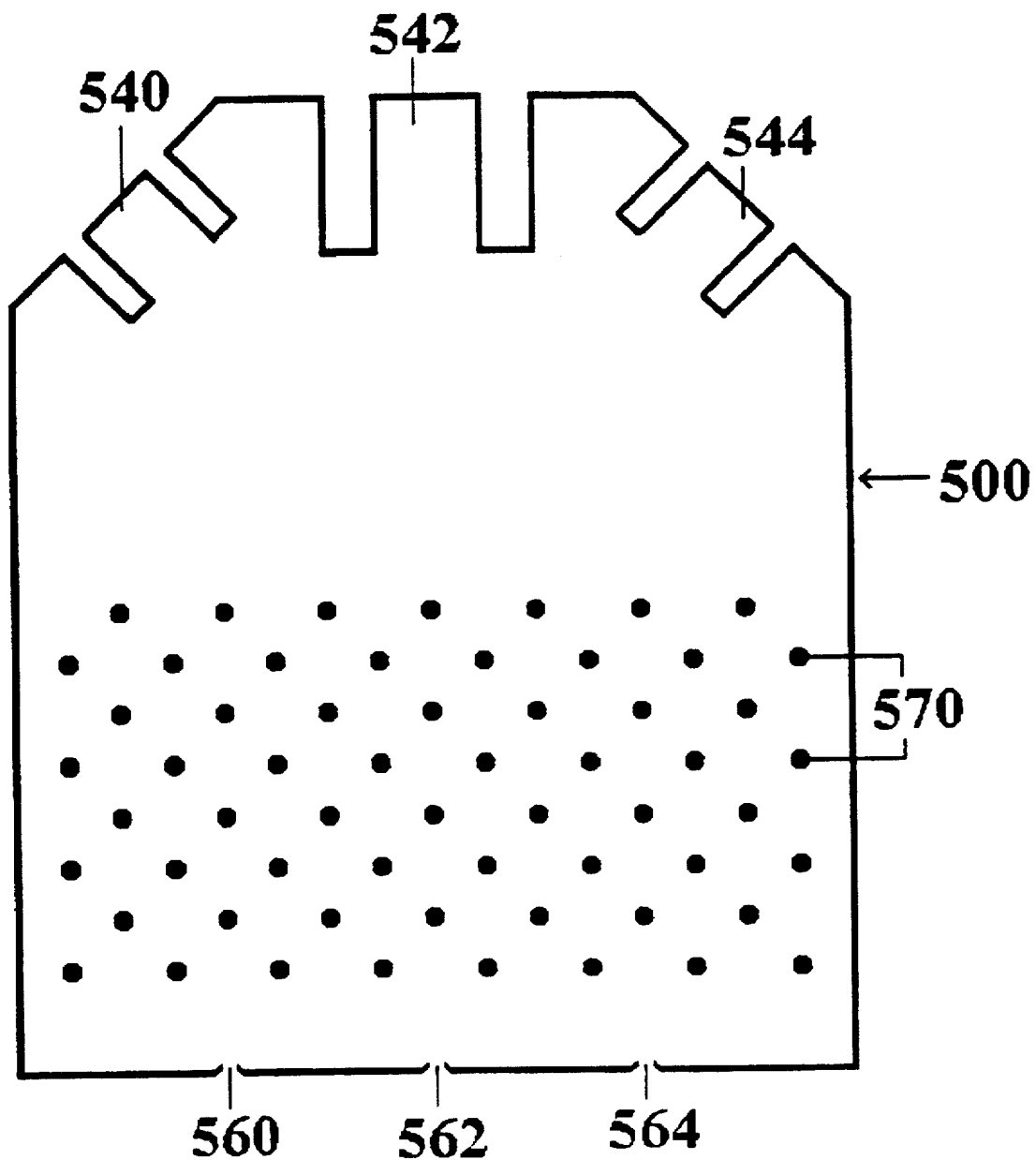
FIG. 5 is a plan view of a blanket for a forced warm air convection system for use primarily in the operating room showing the sheet having perforations according to an embodiment of the present invention.

FIG. 5 is a plan view of a blanket, generally designated by reference numeral 500, for a forced air convection system, wherein the blanket 500, is appropriate for use primarily in the operating room. In particular, FIG. 5 shows a preferred embodiment of the present invention, wherein perforations 570, are formed over only a portion of one sheet of the blanket 500. Perforations 570, may be formed by the same punching procedure described above with respect to blanket 10.

Perforations 570, are formed in off-set rows, such that the perforations 570, in a given row extend across the entire width of the blanket 500, and multiple rows of perforations 570, extend across about half the length of the blanket, beginning at the end of the blanket 500, having exit vents 560, 562, and 564. Adjacent rows of perforations are offset in such a manner that a perforation in any given row occurs midway between adjacent perforations in an adjacent row of perforations. Preferably, the distance between adjacent rows of perforations 570, is about 1 and ⅛ inches and the distance between adjacent perforations 570, in the same row is about 1 and ¼ inches.

The preferred embodiment shown in FIG. 5 provides several advantages associated with providing a warming blanket under a patient. In particular, as noted above, the provision of multiple inlet ports and exit vents, allows the circulating warm air to move through more pathways within the air chamber of the blanket and thus provide a greater and more consistent airflow through the blanket.

In addition, when a warming blanket is provided under a patient, the air exits from the perforations upward and toward the surgical field. It is particularly undesirable to have air exit from perforations in the vicinity of the area of the patient's body upon which a surgical procedure is being carried out. Such exiting air can cause distractions to the surgeon or other surgical team member, and may increase the risk of contamination of the surgical site.

This disadvantage is overcome by providing a blanket as shown in FIG. 5, wherein the perforations 570, are provided along only half of the length of the blanket 500. In particular, the blanket 500, may be positioned under the patient in such a manner that the perforation 570, are under areas of the patient's body that are not in the area of the surgical site. It should be noted that the blanket 500, can be positioned such that inlet ports 540, 542, and 544 are at the feet or at the head of the patient, thereby allowing the perforations 570, selectively positioned under the desired portion of the patient's body.

When using the blanket 500, warming therapy is provided in two ways to the patient. In the area where perforations 570, exist, warming is done primarily by convective means, i.e. by the escape of warm air through perforations 570, toward the patient. In the areas where there are no perforations, the patient is warmed primarily by conductive and radiant transfer of warmth through the blanket 500, material to the patient.

In a more preferred embodiment, a sheet (not shown) may be placed over the patient to trap the warm air being expelled from the perforations 570. The sheet may be of any appropriate material, but preferably is made of disposable plastic.

In this way, warm air that would normally provide no heating to the patient, such as the air escaping from perforation 570, which are distant from any portion of the patient's body, can aid in the heat transfer to the patient. Also, the sheet may include an adhesive such as surgical tape along at least one side for attachment to the blanket 500, or the patient as may be appropriate, in such a manner as to restrict air flow to the surgical site. Therefore, the risk of contamination to the surgical site can be further reduced. In a most preferred embodiment, the sheet is a clear plastic cover which provides all of the advantages above, and in addition allows access and visibility to areas of the patient that are covered.

Several features of the present invention are generic in nature, but may have been described and shown in only one of the drawings. Therefore, the following provides further description of such generic features.

The blankets according to the present invention should be of a size which accommodates pediatric patients comfortably, but without too much excess which could get in the way during hospital procedures. In particular, if the blanket is to be used over the patient, the uninflated blanket should be from about 24 inches to about 36 inches wide and from about 50 inches to about 64 inches long. Preferably, an uninflated blanket for use over the patient is about 30 inches wide and about 57 inches long. Once inflated, the blanket will have somewhat smaller dimensions as the inflation will act to contract the sides and ends of the blanket. In particular, in the preferred embodiment, the inflated blanket for use over the patient will be abut 26 inches wide and about 50 inches long.

For blankets which will be used over the patient, the use of shoulder extensions may be included to help to secure the blanket during use. The shoulder extensions as described above should be sealed off from the air chamber of the blanket so that the shoulder extensions are non-inflatable. The shoulder extensions may extend from either end of the blanket, but preferably extend from the end of the blanket opposite from the inlet port or ports. Preferably, the shoulder extensions are about 10 inches wide and about 7 inches long.

For blankets which will be used under the patient, the uninflated blanket should be from about 20 inches to about 30 inches wide and from about 35 inches to about 47 inches long. In a preferred embodiment, an uninflated blanket for use under the patient is about 25 inches wide and abut 41 inches long. In the preferred embodiment, the inflated blanket for use under the patient will be about 22 inches wide and abut 35 inches long.

Some blankets described above have been shown with a single inlet port and some with multiple, i.e. three inlet ports. By providing a blanket with multiple inlets, the user has the choice of positioning the air supply or blower unit and the supply hose at various locations depending upon the need to access the surgical site. In particular, the inlet used may be optimally chosen to cause the least amount of interference with access to the surgical site. In addition, by providing resealable inlet ports, the user may actually switch inlets during use which may be particularly advantageous in allowing the surgeon full access to the patient during the surgical procedure.

Further, while the present invention has been particularly described by reference to a blanket having one or three inlets, it will be evident to one skilled in the art that any number of inlets could be provided to enable even greater flexibility of use. The placement of additional inlets is limited only by the need to maintain good air distribution and flow within the blanket.

Moreover, it is possible to connect a supply source of warm air to more than one inlet at the same time when using the blanket according to the present invention. This can be accomplished by either connecting different supply sources to different inlets, or alternatively, by connecting a single supply source to multiple inlets using a multiply branched supply hose. For example, if there are two inlets, the supply hose could have a y-shaped configuration. Each of these embodiments of using the present invention, may be advantageous in providing more even heat distribution to all parts of the blanket.

The blankets according to the present invention are all constructed using welds, such as the spot welds noted above to connect the separate sheets of the blanket. The provision of welds provides several advantages, especially for use on pediatric patients. In particular, the welds provide a relatively open air chamber and allows the free flow of warm air in all directions within the blanket. This free air flow provides better heat distribution within the blanket and allow the blankets of the present invention to accomplish the goal of having heat distribution across the blanket vary by less than about 5° C. This is very important in reducing the occurrence of hot or cold spots within the blanket during use. Further, the welds provide additional stability when the blanket is used under the patient. In fact, it has been found that the welds help to prevent the pediatric patient from shifting when placed on top of the blanket and may also eliminate the need for using further materials under the patient for support and cushioning.

In general, for blankets which will be used over the patient, the spot welds noted above may be provided in off set rows across the entire width and along the entire length of the blanket. Adjacent rows of spot welds are offset in such a manner that a spot weld in any given row occurs midway between adjacent spot welds in an adjacent row of spot welds. Preferably, for blankets which will be used over the patient, the distance between adjacent rows of spot welds is about 3 inches and the distance between adjacent spot welds in the same row is about 3 inches.

For blankets which will be used under the patient, spot welds may also be provided in off set rows across the entire width and along the entire length of the blanket. Adjacent rows of spot welds are offset in such a manner that a spot weld in any given row occurs midway between adjacent spot welds in an adjacent row of spot welds. However, for blankets for use under a patient the spacing of the spot welds should be provided in a somewhat tighter pattern. The closer spacing of the spot welds increases the stability of the blanket and reduces shifting of the patient on the blanket as noted above. Preferably, for blankets which will be used under the patient, the distance between adjacent rows of spot welds is about 2 and ½ inches and the distance between adjacent spot welds in the same row is abut 2 and ½ inches.

In one embodiment according to the present invention, certain spot welds may be eliminated. By leaving out certain spot welds, the distribution of air may be directed more thoroughly within the blanket and temperature distribution may be made more uniform and consistent. This can be very advantageous in reducing the occurrence of hot or cold spots within the blanket during use.

The blankets according to the present invention may be formed of any suitable material capable of being sealed together at selected positions and having sufficient strength to allow inflation and adequate air distribution within the inflated air chamber. Such materials include plastics, natural fibers and synthetic blends; such as cotton, wool, silk, rayon, polypropylene, cotton and polyester blends, polyester and cellulose blends, rayon and polyester blends, non-woven wood pulp compositions, laminated plastic and wood pulp materials, and combinations thereof.

In addition, it should be noted that the blankets may be formed of various laminated layers of the above materials. For example, each sheet of the blankets according to the present invention, could be a two or three ply layer of material.

In another embodiment of the present invention, the convective air warming blankets may be treated with a fire retardant material. In particular, the blankets may be treated by a spraying, coating, or other appropriate technique, with the fire retardant material. Such treatment produces advantageous blankets which are both nonflammable and laser resistant. The fire retardant spray may be any suitable spray which will render the blanket nonflammable and laser resistant. Such a spray my be used regardless of the material from which the blanket is made. One material which has been found to be useful as a fire retardant spray for convective air warming blankets is available from Project Fire Safety, Inc. and is identified as product number MG 702. The treatment of blankets to render them nonflammable and laser resistant is applicable to pediatric and adult sized blankets, as well as any other size that may be desired.

It should be noted that while particular blankets described above have been identified for use primarily in the operating room or for use primarily outside the operating room, that it will be evident to one skilled in the art that any of the blankets according to the present invention could be used in areas other than the primarily indicated area. For example, a blanket for use primarily in the operating room, could also be used outside the operating room, such as in the PACU, ICU or regular hospital room, and vice versa. Further, any of the blankets described herein could also be used in a nursing home, patient's home or any place where hypothermia is a problem.

The blankets according to the present invention have been described as being useful in the prevention and treatment of hypothermia. It will be evident to one skilled in the art that a source of pressurized cooled air or room temperature air could also be provided to the blankets according to the present invention to control body temperature of the patient under conditions of hyperthermia.

The foregoing has been a description of certain preferred embodiments of the present invention, but is not intended to limit the invention in any way. Rather, many modifications, variations and changes in details may be made within the scope of the present invention.

What is claimed is:

1. A method of preventing hyperthermia in pediatric patients, said method comprising:
   providing a blanket which may be used with a forced air convection system, wherein such blanket is sized to accommodate a pediatric patient;
   placing said blanket under the patient;
   connecting said blanket to a supply source of forced cool air cooler than ambient air; and supplying said forced cool air from said supply source to said blanket such that the cool air temperature distribution across the blanket varies by less than 5° C. wherein said blanket has a surface which contacts said patient when said blanket is placed under said patient, wherein the patient-contacting surface has perforations through which said cool air exits said blanket, wherein the patient-contacting surface has said perforations only in about one-half a length of the patient contacting surface, wherein about half the patient-contacting surface is unperforated.

2. A method according to claim 1, further including:
   providing a sheet having an adhesive along at least one end;
   placing said sheet over the patient positioned on said blanket; and
   adhesively connecting said sheet to said blanket, the patient, or both.

3. A method according to claim 2, wherein the step of providing includes providing a clear plastic sheet.

4. A method according to claim 1, wherein said blanket includes multiple inlet ports formed along one end of said blanket; and wherein said step of supplying forced cool air comprises:
   supplying forced cool air from said supply source to said blanket through only one of said multiple inlet ports.

5. A method according to claim 1, wherein said blanket includes multiple inlet ports formed along one end of said blanket; and wherein said step of supplying forced cool air comprises:
   supplying forced cool air from said supply source to said blanket through more than one of said multiple inlet ports.

6. The method of claim 1, including, providing a sheet having an adhesive along at least an edge of the sheet, placing the sheet over the patient and the perforated portion of the patient-contacting surface, and adhesively attaching the sheet to at least one of the patient or the blanket.

7. A method of preventing hypothermia in pediatric patients, comprising:
   a) providing a blanket for use with a forced air convection system, wherein said blanket is sized to accommodate a pediatric patient, said blanket including multiple inlet ports formed along one end of said blanket;
   b) placing said blanket under said pediatric patient;
   c) providing a sheet having an adhesive along at least one end of the sheet;
   d) placing said sheet over the pediatric patient positioned on said blanket;
   e) adhesively connecting said sheet to at least one of said blanket or said pediatric patient; and wherein said blanket has a surface which contacts said patient when said blanket is placed under said patient, wherein the patient-contacting surface has perforations through which said warm air exits said blanket, wherein the patient-contacting surface has said perforations only in about one-half a length of the patient contacting surface, wherein about half the patient-contacting surface is unperforated,
   f) connecting said blanket to a supply source of forced warm air, which forced warm air is warmer than ambient air, and supplying said forced warm air from said supply source to said blanket such that warm air distribution across said blanket varies by less than 5° C.,
   wherein said blanket has a surface which contacts said patient when said blanket is placed under said patient, wherein the patient-contacting surface has perforations through which said warm air exits said blanket, wherein the patient-contacting surface has said perforations only in about one-half a length of the patient contacting surface, wherein about half the patient-contacting surface is unperforated.

8. The method of claim 7, wherein said sheet is placed over the patient and over the perforated portion of the patient-contacting surface.

9. A method of preventing hypothermia in pediatric patients, said method comprising:

provididing a blanket which may be used with a forced air convection system, wherein such blanket is sized to accommodate a pediatric patient;

placing said blanket under a patient;

connecting said blanket to a supply source of forced warm air warmer than ambiant; and supplying said forced warm air from said supply source to said blanket such that the warm air temperature distribution across the blanket varies by less than 5° C., wherein said blanket has a surface which contacts said patient when said blanket is placed under said patient, wherein the patient-contacting surface has perforations through which said warm air exits said blanket, wherein the patient-contacting surface has said perforations only in about one-half a length of the patient contacting surface, wherein about half the patient-contacting surface is unperforated.

10. The method of claim 9, including, providing a sheet having an adhesive along at least an edge of the sheet, placing the sheet over the patient and the perforated portion of the patient-contacting surface, and adhesively attaching the sheet to at least one of the patient or the blanket.

11. A method according to claim 9, further including:

providing a sheet having an adhesive along at least one end;

placing said sheet over the patient positioned on said blanket; and adhesively connecting said sheet to said blanket or the patient, or both.

12. A method according to claim 11, wherein the step of providing includes providing a clear plastic sheet.

13. A method according to claim 9, wherein said blanket includes multiple inlet ports formed along one end of said blanket; and wherein said step of supplying forced warm air comprises:

supplying forced warm air from said supply source to said blanket through only one of said multiple inlet ports.

14. A method according to claim 9, wherein said blanket includes multiple inlet ports formed along one end of said blanket; and wherein said step of supplying forced warm air comprises:

supplying forced warm air from said supply source to said blanket through more than one of said multiple inlet ports.

\* \* \* \* \*